United States Patent
Tanabe

(10) Patent No.: US 8,057,699 B2
(45) Date of Patent: Nov. 15, 2011

(54) POLYMERIZABLE LIQUID CRYSTAL COMPOSITION AND USES FOR THE SAME

(75) Inventor: Mayumi Tanabe, Ichihara (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 12/779,775

(22) Filed: May 13, 2010

(65) Prior Publication Data
US 2010/0219374 A1    Sep. 2, 2010

Related U.S. Application Data

(62) Division of application No. 11/819,663, filed on Jun. 28, 2007, now Pat. No. 7,744,776.

(30) Foreign Application Priority Data

Jun. 29, 2006  (JP) .................................. 2006-180389
May 16, 2007  (JP) .................................. 2007-130971

(51) Int. Cl.
*C09K 19/38* (2006.01)
*C09K 19/36* (2006.01)

(52) U.S. Cl. ................................. 252/299.01; 252/299.7

(58) Field of Classification Search ............. 252/299.01, 252/299.5, 299.7
See application file for complete search history.

(56) References Cited

U.S. PATENT DOCUMENTS

| | | | |
|---|---|---|---|
| 4,637,896 A | 1/1987 | Shannon | 252/299 |
| 5,798,147 A | 8/1998 | Beck et al. | 427/511 |
| 7,744,776 B2 * | 6/2010 | Tanabe | 252/299.7 |

FOREIGN PATENT DOCUMENTS

| | | |
|---|---|---|
| GB | 2132623 A | 7/1984 |
| JP | 08-024625 | 1/1996 |
| WO | WO 97/30136 | 8/1997 |
| WO | WO 2006/128090 A2 | 11/2006 |
| WO | WO 2006/128091 A2 | 11/2006 |

* cited by examiner

*Primary Examiner* — Shean Wu
(74) *Attorney, Agent, or Firm* — Hogan Lovells US LLP

(57) ABSTRACT

The polymerizable liquid crystal composition includes at least two selected from the group of compounds represented by the following Formulas (1) and (2):

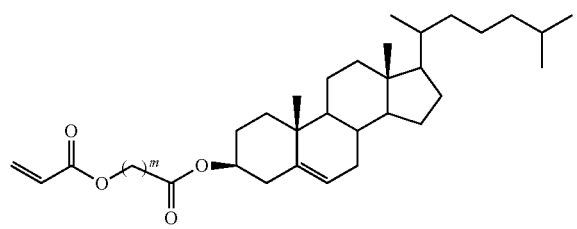

wherein m is 5 or 10; and

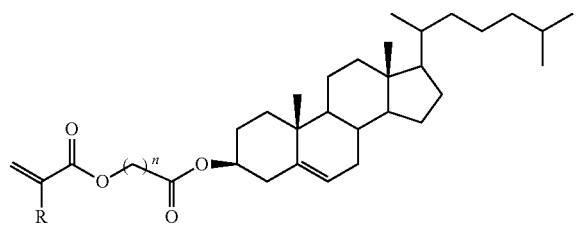

wherein n is 3, 4, 6, 7, 8 or 9, and R is hydrogen or methyl
wherein said composition includes at most only two compounds of Formula (1) in which m is 10; and
wherein said composition does not include a compound of Formula (2) in which n is 3 and R is hydrogen.

22 Claims, No Drawings

POLYMERIZABLE LIQUID CRYSTAL COMPOSITION AND USES FOR THE SAME

CROSS REFERENCE TO RELATED APPLICATIONS

This application is a divisional of application Ser. No. 11/819,663, filed on Jun. 28, 2007, the entire contents of which are incorporated herein by reference. This application also claims priority under 35 U.S.C. §119 to Japanese Patent Application Nos. JP 2006-180389 (filed Jun. 29, 2006) and JP 2007-130971 (filed May 16, 2007), which applications are expressly incorporated herein by reference in their entirety.

BACKGROUND OF THE INVENTION

1. Field of the Invention

The invention relates to a polymerizable liquid crystal composition and uses for the same, more specifically to a polymerizable liquid crystal composition which reflects light of a specific wavelength in the vicinity of room temperature, a polymer including the above composition and uses for the above polymer.

2. Related Art

A cholesteric liquid crystal molecule has a spiral structure in a liquid crystal state. Accordingly, when a cholesteric liquid crystal phase is irradiated with light, it reflects a circular polarizing light of a specific wavelength corresponding to a spiral rotational direction of the liquid crystal molecule and a length of the pitch. For example, when irradiated with a visible light, it reflects selectively lights having wavelengths of blue, green, yellow and red corresponding to a length of a pitch in the liquid crystal. The color tones thereof are different from those of pigments and dyes which take on colors by absorption of lights and have a visual dependency in which a color tone changes according to viewing angles. Further, a length of a pitch in cholesteric liquid crystal can be controlled by temperature and the kind of compounds, and therefore it can selectively reflect not only visible lights but also lights of near infrared and ultraviolet regions.

There have been materials which selectively reflect lights of various wavelengths in a broad wavelength region making use of the characteristics of the cholesteric liquid crystal. They are, for example, liquid crystal pigments, coating materials, spray inks, print inks, cosmetics, printed matters for preventing counterfeit, ornamental articles and the like. Further, they are proposed as well for polarizing plates in optical devices such as liquid crystal displays and holographic devices, compensation plates, optical films such as color filters and the like. In the case of a cholesteric liquid crystal pigment which is an existing material, flake-shaped cholesteric liquid crystal polymers and microencapsulated cholesteric liquid crystal are used. The uses thereof include coating materials for cars, cosmetic ingredients and the like.

A polymer of a mixture including a chiral polymerizable mesogen compound having an optically active group, a non-chiral polymerizable mesogen compound, a photoinitiator and the like is described as a pigment which is processed in a flake form in JP 2000-505485 T (Patent Document 1; WO 97/30136). In Patent Document 1, the kind of chiral polymerizable mesogen compound and the content thereof in the mixture are changed to thereby control the pitch in a spiral of cholesteric liquid crystal and obtain a pigment having a desired color tone.

Further, a microencapsulated liquid crystal material is described in JP H8-24625 A/1996 (Patent Document 2). The above material has a structure in which a copolymer of glutamic γ-ester having a thermotropic cholesteric liquid crystallinity is covered with a film including an epoxy resin and amine as structural components. The glutamic γ-ester copolymer has a high cohesive property and therefore has to be aligned by applying a shearing stress after being molten in order to solidify it. In Patent Document 2, however, cohesion can be avoided by microencapsulation, and the operability in solidification is enhanced.

The above flake-shaped or microencapsulated liquid crystal material is used as a color material for coating materials, ink components and cosmetic ingredients. However, a flake-shaped pigment used as a color material is produced by forming a cholesteric polymer layer on a support, peeling it and then crushing the polymer layer. A microcapsule is produced by forming a resin coating film on a cholesteric liquid crystal material. Further, a process of a multistage in which they are dispersed once in a solvent, coated on an object material and fixed is required.

In contrast with this, in JP H10-508882 T/1998 (Patent Document 3; U.S. Pat. No. 5,798,147), a composition including a polymerizable liquid crystal monomer and a chiral liquid crystal monomer or a chiral non-liquid crystal monomer is applied directly or after being dissolved in a solvent on a support at a relatively low temperature, and it is then cured by an energy beam. In Patent Document 3, a composition including a mixture of tricyclic liquid crystalline compounds in which a nematic phase area is 90° C. or higher and a chiral monomer is used in examples. Further, in mixing the respective components of the composition, they are dissolved in dichloromethane and then subjected once to heat treatment up to 70° C. A cholesteric material which is a color material preferably exhibits a stable cholesteric liquid crystal phase in the vicinity of room temperature in order to carry out coating and print treatment in the vicinity of room temperature of a relatively low temperature.

A composition including 2 to 3 components of polymerizable liquid crystal monomers which are cholesterol derivatives is described as the above material in JP S59-109505 A/1984 (Patent Document 4; U.S. Pat. No. 4,637,896). Among them, a 1:1 mixture of a compound Va and a compound Ve each described in Example 7 exhibits a cholesteric phase in a wide temperature range and realizes fixation of cholesteric colors of blue, green and orange by photocuring in a range of 10 to 32° C. in the vicinity of room temperature. In the method of the Patent Document 4, however, the temperature of the materials has to be controlled at an interval of 5° C. in curing in order to obtain the targeted polymer, and a polymer which takes on specific reflected colors of red, green and blue at a fixed room temperature has not been obtained.

SUMMARY OF THE INVENTION

The invention relates to a polymerizable liquid crystal composition including at least two selected from the group of compounds represented by Formulas (1) and (2):

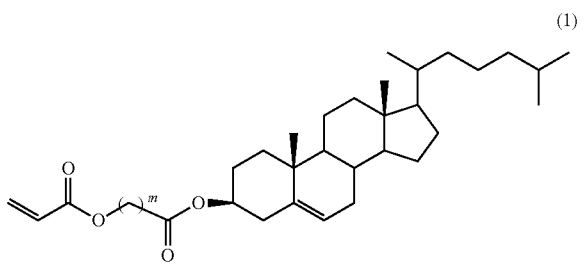

(1)

wherein m is 5 or 10; and

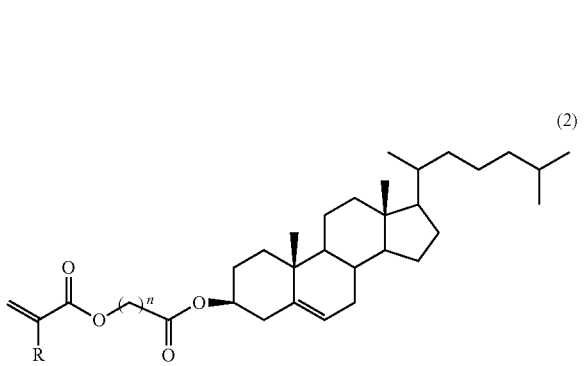

(2)

wherein n is 3, 4, 6, 7, 8 or 9, and R is hydrogen or methyl;
wherein said composition includes at most two compounds of Formula (1) in which m is 10; and
wherein said composition does not include a compound of Formula (2) in which n is 3 and R is hydrogen.

DETAILED DESCRIPTION OF THE INVENTION

The first object of the invention is to provide a polymerizable liquid crystal composition showing a cholesteric phase in the vicinity of room temperature. The second object of the invention is to control a reflected color in a cholesteric reflection zone over a wide range of red, green, blue and purple by changing the constitution of the composition. The third object thereof is to form and fix a coating film exhibiting a cholesteric liquid crystal phase directly on a substrate which is an object of cholesteric liquid crystal.

It has been observed that the problems described above can be solved by applying a composition including two or more kinds of specific polymerizable liquid crystal compounds on the surface of a substrate which is an object and curing it by heat and/or light. The invention includes:

[1] A polymerizable liquid crystal composition including at least two selected from the group of compounds represented by Formulas (1) and (2):

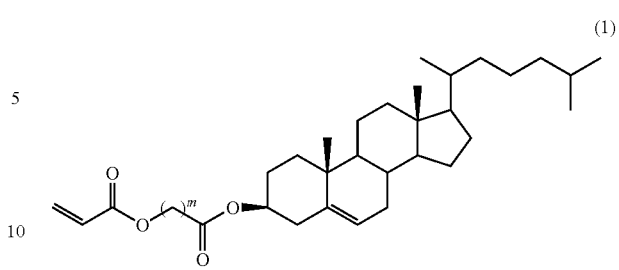

(1)

wherein m is 5 or 10; and (2)

wherein n is 3, 4, 6, 7, 8 or 9, and R is hydrogen or methyl;
wherein said composition includes at most two compounds of Formula (1) in which m is 10; and
wherein said composition does not include a compound of Formula (2) in which n is 3 and R is hydrogen.

[2] The polymerizable liquid crystal composition as described in item [1], further including at least one compound selected from the group of compounds represented by Formulas (3), (4) and (10):

(3)

wherein p is 5 or 10;

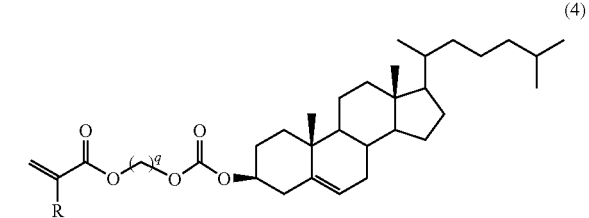

(4)

wherein q is 2, 4 or 6, and R is hydrogen or methyl; and

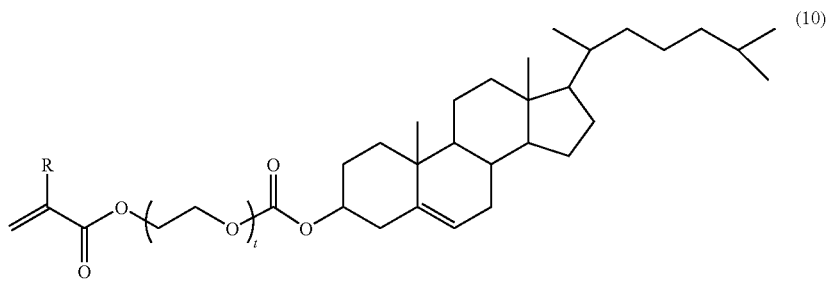

wherein t is 2, 3 or 4, and R is hydrogen or methyl.

[3] The polymerizable liquid crystal composition as described in item [1], including the compound in which m is 5 in Formula (1) and the compound in which n is 3 and R is hydrogen in Formula (2).

[4] The polymerizable liquid crystal composition as described in item [1], including the compound in which m is 5 in Formula (1), the compound in which m is 10 in Formula (1) and the compound in which n is 3 and R is hydrogen in Formula (2).

[5] The polymerizable liquid crystal composition as described in item [1], including the compound in which m is 5 in Formula (1) and the compound in which n is 4 and R is hydrogen in Formula (2).

[6] The polymerizable liquid crystal composition as described in item [1], including the compound in which m is 5 in Formula (1) and the compound in which m is 10 in Formula (1).

[7] The polymerizable liquid crystal composition as described in item [2], including the compound in which m is 5 in Formula (1), the compound in which n is 3 and R is hydrogen in Formula (2) and the compound in which q is 2 and R is hydrogen in Formula (4).

[8] The polymerizable liquid crystal composition as described in item [2], including the compound in which m is 5 in Formula (1), the compound in which m is 10 in Formula (1) and the compound in which q is 2 and R is methyl in Formula (4).

[9] The polymerizable liquid crystal composition as described in item [2], including the compound in which m is 5 in Formula (1), the compound in which n is 3 in Formula (2) and the compound in which t is 2 in Formula (10).

[10] The polymerizable liquid crystal composition as described in item [2], including the compound in which m is 5 in Formula (1), the compound in which n is 3 in Formula (2) and the compound in which t is 3 in Formula (10).

[11] The polymerizable liquid crystal composition as described in item [2], including the compound in which m is 5 in Formula (1), the compound in which n is 3 in Formula (2) and the compound in which t is 4 in Formula (10).

[12] A polymerizable liquid crystal composition including at least one selected from the group of compounds represented by Formula (5) and at least one selected from the group of compounds represented by Formula (6):

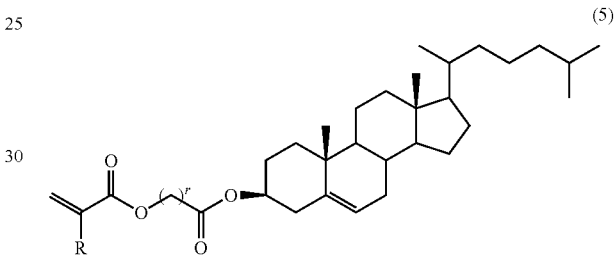

wherein r is an integer of 3 to 9, and R is hydrogen or methyl; and

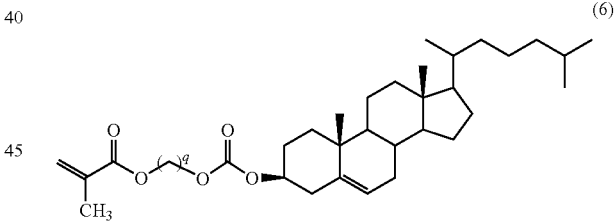

wherein q is 2, 4 or 6.

[13] The polymerizable liquid crystal composition as described in item [12], further including at least one selected from the group of compounds represented by Formula (10):

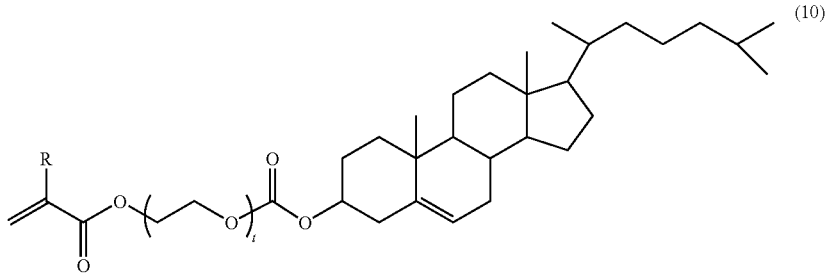

wherein t is 2, 3 or 4, and R is hydrogen or methyl.

[14] The polymerizable liquid crystal composition as described in item [13], including the compound in which r is 5 in Formula (5), the compound in which q is 2 in Formula (6) and the compound in which t is 2 in Formula (10).

[15] The polymerizable liquid crystal composition as described in item [13], including the compound in which r is 5 in Formula (5), the compound in which q is 4 in Formula (6) and the compound in which t is 2 in Formula (10).

[16] The polymerizable liquid crystal composition as described in item [13], including the compound in which r is 5 in Formula (5), the compound in which q is 2 in Formula (6) and the compound in which t is 3 in Formula (10).

[17] The polymerizable liquid crystal composition as described in the item [13], including the compound in which r is 5 in Formula (5), the compound in which q is 4 in Formula (6) and the compound in which t is 3 in Formula (10).

[18] The polymerizable liquid crystal composition as described in item [12], further including at least one selected from the group of compounds represented by Formulas (7) and (8):

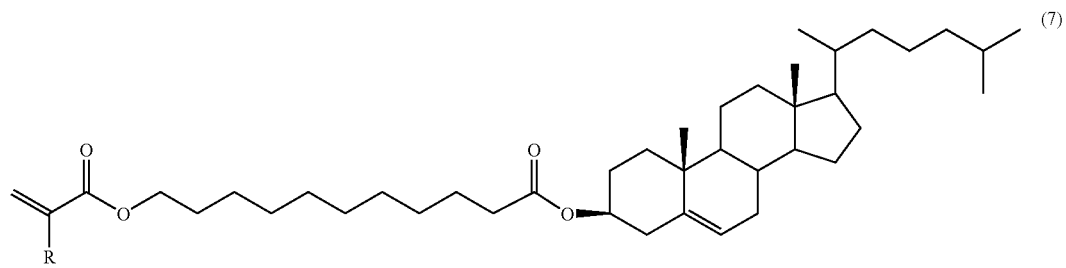

wherein R is hydrogen or methyl; and

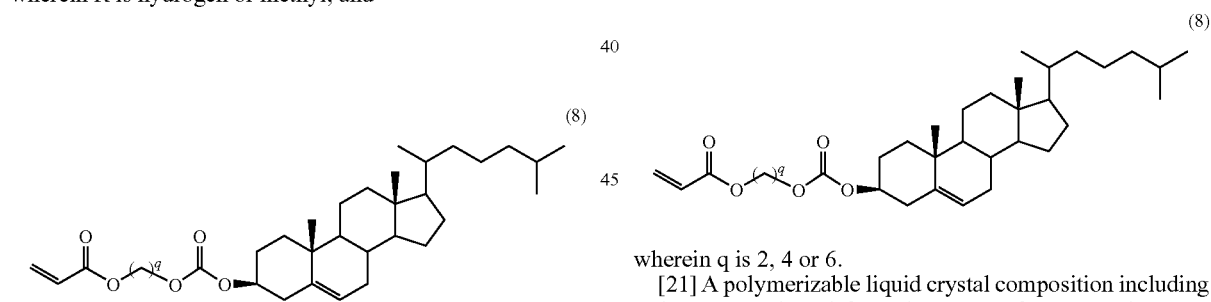

wherein q is 2, 4 or 6.

[19] The polymerizable liquid crystal composition as described in the above item [12], including the compound in which r is 5 and R is hydrogen in Formula (5) and the compound in which q is 2 in Formula (6).

[20] A polymerizable liquid crystal composition including at least one selected from the group of compounds represented by Formula (9), at least one selected from the group of compounds represented by Formula (8) and at least one selected from the group of multifunctional (meth)acryl monomers and (meth)acryl oligomers:

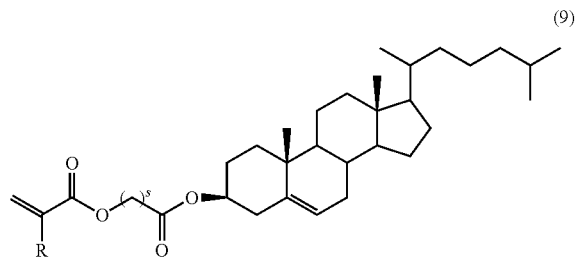

wherein s is an integer of 3 to 10, and R is hydrogen or methyl; and

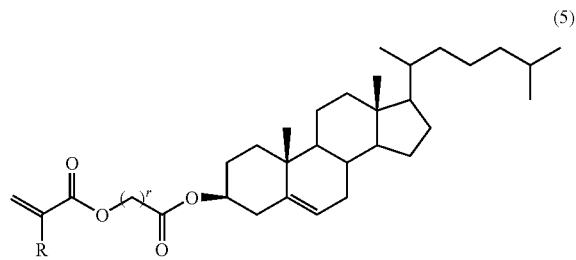

wherein q is 2, 4 or 6.

[21] A polymerizable liquid crystal composition including at least one selected from the group of compounds represented by Formula (5) and at least one selected from the group of compounds represented by Formula (10):

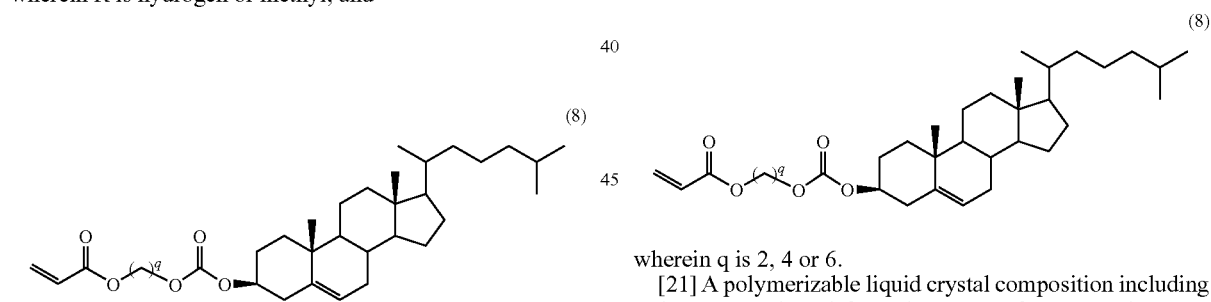

wherein r is an integer of 3 to 9, and R is hydrogen or methyl; and

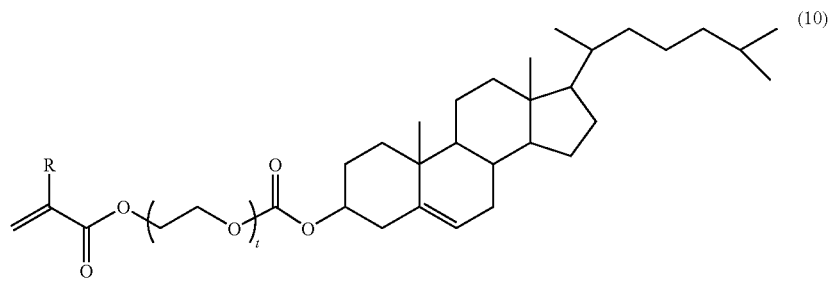

wherein t is 2, 3 or 4, and R is hydrogen or methyl.

[22] The polymerizable liquid crystal composition as described in item [21], including the compound in which r is 3 in Formula (5) and the compound in which t is 3 in Formula (10).

[23] The polymerizable liquid crystal composition as described in item [21], including the compound in which r is 5 in Formula (5) and the compound in which t is 2 in Formula (10).

[24] The polymerizable liquid crystal composition as described in item [21], including the compound in which r is 5 in Formula (5) and the compound in which t is 3 in Formula (10).

[25] The polymerizable liquid crystal composition as described in item [21], including the compound in which r is 5 in Formula (5) and the compound in which t is 4 in Formula (10).

[26] The polymerizable liquid crystal composition as described in item [21], further including at least one selected from the group of compounds represented by Formula (4):

wherein q is 2, 4 or 6, and R is hydrogen or methyl.

[27] The polymerizable liquid crystal composition as described in item [26], including the compound in which r is 3 in Formula (5), the compound in which t is 3 in Formula (10) and the compound in which q is 4 in Formula (4).

[28] The polymerizable liquid crystal composition as described in item [26], including the compound in which r is 5 in Formula (5), the compound in which t is 3 in Formula (10) and the compound in which q is 2 in Formula (4).

[29] A polymerizable liquid crystal composition including at least one selected from the group of compounds represented by Formula (4) and at least one selected from the group of compounds represented by Formula (10):

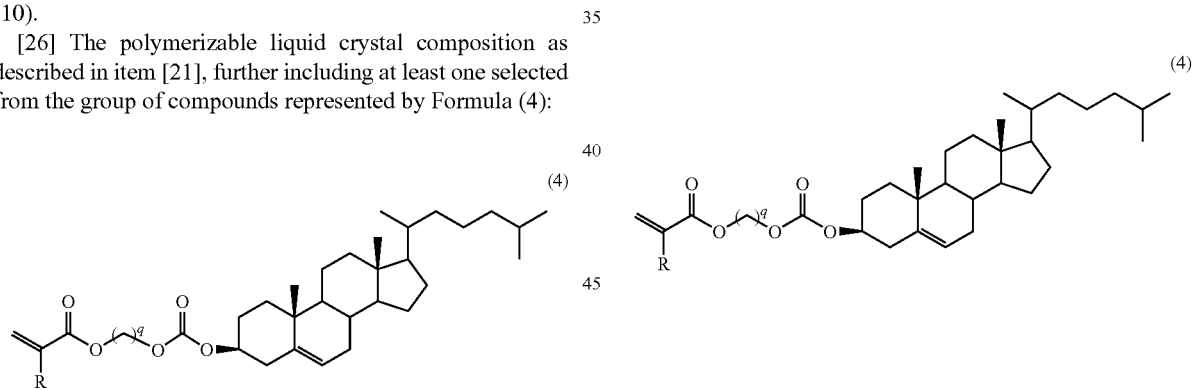

wherein q is 2, 4 or 6, and R is hydrogen or methyl; and

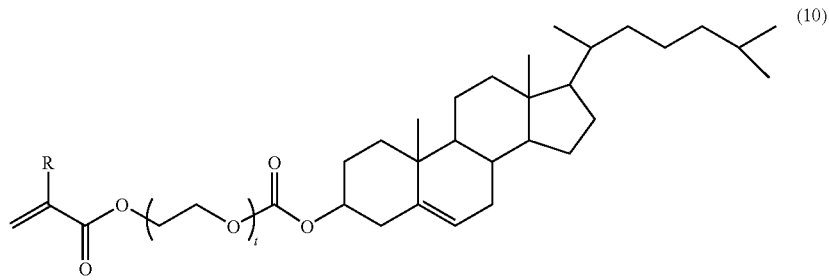

wherein t is 2, 3 or 4, and R is hydrogen or methyl.

[30] The polymerizable liquid crystal composition as described in item [29], including the compound in which q is 2 in Formula (4) and the compound in which t is 2 in Formula (10).

[31] The polymerizable liquid crystal composition as described in the above item [29], including the compound in which q is 2 in Formula (4) and the compound in which t is 3 in Formula (10).

[32] The polymerizable liquid crystal composition as described in item [29], including the compound in which q is 4 in Formula (4) and the compound in which t is 2 in Formula (10).

[33] The polymerizable liquid crystal composition as described in item [29], including the compound in which q is 4 in Formula (4) and the compound in which t is 3 in Formula (10).

[34] The polymerizable liquid crystal composition as described in any of items [1] to [19] and [21] to [33], further including a non-liquid crystalline polymerizable compound.

[35] The polymerizable liquid crystal composition as described in item [34], wherein the non-liquid crystalline polymerizable compound is at least one selected from the group of monofunctional (meth)acryl monomers, multifunctional (meth)acryl monomers and (meth)acryl oligomers.

[36] A cosmetic ingredient including the polymerizable liquid crystal composition as described in any of items [1] to [35].

[37] A printing ink including the polymerizable liquid crystal composition as described in any of items [1] to [35].

[38] A UV curing type printing ink including the polymerizable liquid crystal composition as described in any of items [1] to [35].

[39] A polymer obtained by polymerizing the polymerizable liquid crystal composition as described in any of items [1] to [35].

[40] The polymer as described in the above item [39], exhibiting a cholesteric liquid crystal phase.

[41] A membrane including the polymer as described in items [39] or [40].

[42] A film including the polymer as described in items [39] or [40].

[43] A cosmetic ingredient including the polymer as described in items [39] or [40].

[44] A color material including the polymer as described in items [39] or [40].

[45] Use of the polymer as described in items [39] or [40] for applications selected from liquid crystal pigments, coating materials, spray inks, print inks, cosmetics, printed matters for preventing counterfeit, ornamental articles, toys and optical films.

According to the invention, a polymerizable liquid crystal composition is obtained which exhibits a cholesteric phase in the vicinity of room temperature and can control a reflected color in a cholesteric reflection zone over a wide range of red, green, blue and purple by changing the composition, and which can be applied directly on an object matter to form and fix a coating film. Accordingly, a multistage operation in which a cholesteric polymer which is a polymerized matter is crushed to a flake form and in which cholesteric liquid crystal is microencapsulated, mixed again with a solvent and applied is not required.

The polymerizable liquid crystal composition according to the invention, a polymer made from the composition and uses thereof shall be explained below in details. As used herein, the polymerizable liquid crystal compound represented by Formula (1) shall be referred to as the "compound (1)," and the compounds represented by the other formulas shall be referred to in the same abbreviation. The meaning of "liquid crystalline" shall not be restricted only to having a liquid crystal phase, and the characteristic that a compound itself does not have a liquid crystal phase but can be used as a component for a liquid crystal composition when mixed with other liquid crystal compounds is included as well in the meaning of "liquid crystalline."

Polymerizable Liquid Crystal Composition

The polymerizable liquid crystal composition according to the invention includes: as the first embodiment, a composition including at least two monofunctional liquid crystalline acrylate compounds selected from the group of the compound (1) and the compound (2) as essential components (hereinafter referred to as the "composition (I)"); as the second embodiment, a composition including at least one compound selected from the compounds (5) and at least one selected from the compounds (6) (hereinafter referred to as the "composition (II)"); as the third embodiment, a composition including at least one compound selected from the compounds (9), at least one compound selected from the compounds (8) and at least one compound selected from the group of multifunctional (meth)acrylates and (meth)acryl oligomers (hereinafter referred to as the "composition (III)"); as the fourth embodiment, a composition including at least one s compound elected from the compounds (5) and at least one compound selected from the compounds (10) (hereinafter referred to as the "composition (IV)"); and as the fifth embodiment, a composition including at least one compound selected from the compounds (4) and at least one compound selected from the compounds (10) (hereinafter referred to as the "composition (V)"). The polymerizable liquid crystal composition of the invention has a broad cholesteric liquid crystal phase in the vicinity of room temperature (about 10 to 40° C.), and a wavelength region of light reflected by the cholesteric phase can be controlled by changing the composition ratios of the respective structural components and the temperature in curing the composition, which make it possible to form a polymer reflecting light of a wavelength according to the desired colors and the purposes.

Composition (I)

The composition (I) of the invention includes as essential components, at least two monofunctional liquid crystalline acrylate compounds selected from the group of the compound (1) and the compound (2). However, excluded is a combination including only two kinds of a compound in which m is 10 in Formula (1) described above and a compound in which n is 3 and R is hydrogen in Formula (2) described above. Accordingly, combination including of a compound in which m is 10 in Formula (1) described above, a compound in which n is 3 and R is hydrogen in Formula (2) described above and at least one another compound (for example, a compound in which m is 5 in Formula (1) described above) selected from the compounds (1) and (2) belongs to the composition (I) of the invention.

The composition (I) of the invention may further include at least one compound selected from the group of the compound (3), the compound (4) and the compound (10) in addition to the compounds (1) and (2). Further, the composition (I) of the invention may include a polymerizable compound (hereinafter referred to as the "other polymerizable compound") other than the compounds (1) to (4), a non-polymerizable component, an organic solvent and the like.

A preferred embodiment of the composition (I) of the invention includes, for example: the combination of the compound in which m is 5 in Formula (1) and the compound in which n is 3 and R is hydrogen in Formula (2); the combination of the compound in which m is 5 in Formula (1), the compound in which m is 10 in Formula (1) and the compound in which n is 3 and R is hydrogen in Formula (2); the combination of the compound in which m is 5 in Formula (1) and the compound in which n is 4 and R is hydrogen in Formula (2); the combination of the compound in which m is 5 in Formula (1) and the compound in which m is 10 in Formula (1); the combination of the compound in which m is 5 in Formula (1), the compound in which n is 3 and R is hydrogen in Formula (2) and the compound in which q is 2 and R is hydrogen in Formula (4); the combination of the compound in which m is 5 in Formula (1), the compound in which m is 10 in Formula (1) and the compound in which q is 2 and R is methyl in Formula (4); the combination of the compound in which m is 5 in Formula (1), the compound in which n is 3 in Formula (2) and the compound in which t is 2 in Formula (10); the combination of the compound in which m is 5 in Formula (1), the compound in which n is 3 in Formula (2) and the compound in which t is 3 in Formula (10); and the combination of the compound in which m is 5 in Formula (1), the compound in which n is 3 in Formula (2) and the compound in which t is 4 in Formula (10).

In respect to the characteristics of the compounds (1) and (2) before polymerization, both are compounds having an optical activity and have large HTP (helical twist power) and a good compatibility with other polymerizable liquid crystal compounds, compositions and solvents, and they can develop spiral pitches according to purposes. The compound (1) exhibits a cholesteric liquid crystal phase in the vicinity of room temperature and shows alone a reflected color including mainly green to blue (purple) colors. The compound (2) is liable to be crystallized alone in the vicinity of room temperature.

In the composition (I) of the invention, at least two compounds selected from the compounds (1) and (2) as essential components are mixed, and the combination of the structural components, the composition ratio thereof or the temperature in curing is changed, whereby a composition is obtained exhibiting a cholesteric phase in a relatively broad temperature area in the vicinity of room temperature.

The contents of the respective components selected from the compounds (1) and (2) in the composition (I) of the invention are usually approximately 2 weight % or more, preferably approximately 5 weight % or more respectively based on approximately 100 weight % of the total of the essential components.

When the composition (I) of the invention contains each at least one of the compounds (1) and the compounds (2), a content of the compound (1) is preferably approximately 40 to approximately 98 weight %, more preferably approximately 50 to approximately 95 weight %, and a content of the compound (2) is preferably approximately 2 to approximately 60 weight %, more preferably approximately 5 to approximately 50 weight % each based on approximately 100 weight % of the total of the essential components.

The compounds (1) and (2) can be synthesized, for example, by the following synthetic schemes.

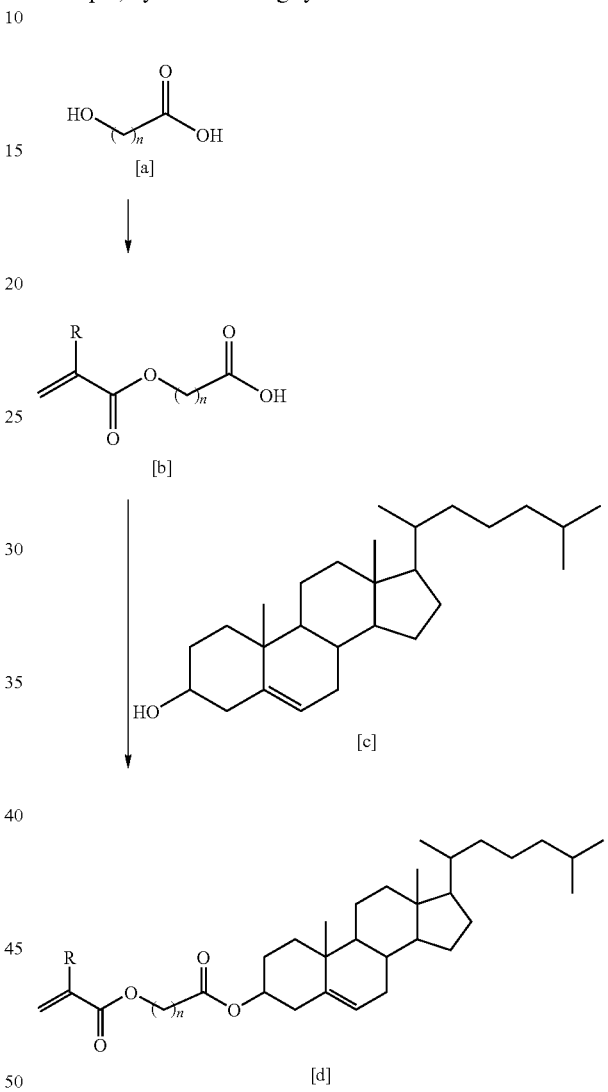

In the synthetic scheme described above, a carboxylic acid derivative [a] having a hydroxy group can be synthesized by a hydrolytic method of lactones described in examples of GB2070596B2 or hydrolysis of halogenated aliphatic carboxylic acid derivatives described in GB2085881A. Also, a carboxylic acid derivative [b] having —OCOCH=CH$_2$ can be synthesized according to a method described in Tetrahedron 60 (51), 11765 to 11770, (2004). A production method of a derivative [d] of cholesterol ester which is a final product is disclosed in Journal of Fluorine Chemistry 109 (2), 205 to 208, (2001).

The synthetic scheme described above shall be explained by showing an example thereof. The compound [a] is obtained by hydrolyzing lactones such as γ-butyrolactone and ε-caprolactone or halogenated fatty acids such as 11-bromoundecanoic acid in an alkaline aqueous solution. The compound [a] obtained is acrylated to obtain the compound [b], and then the compound [b] is subjected to esterification reaction with cholesterol [c], whereby the compound [d] which corresponds to the compound (1) and the like can be synthesized.

The compounds (3), (4) and (10) are optically active compounds as is the case with the compounds (1) and (2), and they have large HTP (helical twist power).

At least one compound selected from the compounds (3), (4) and (10) which is contained in the composition (I) of the invention makes it possible to prevent the composition from being crystallized at room temperature, control a reflected color at a specific temperature and develop a cholesteric phase showing reflected colors of red, orange, green and blue (purple) in a broader temperature region. Specifically, the compound (10) has a high effect in terms of preventing the composition from being crystallized at room temperature.

In the composition (I) of the invention, a content of the component selected from the compounds (3), (4) and (10) is preferably approximately 5 to approximately 60 weight %, more preferably approximately 10 to approximately 50 weight % based on approximately 100 weight % of the total of the compounds (1) to (4) and (10).

The compound (3) can be synthesized by the same method as in the compounds (1) and (2). Further, the compound (4) can be synthesized according to the following synthetic scheme.

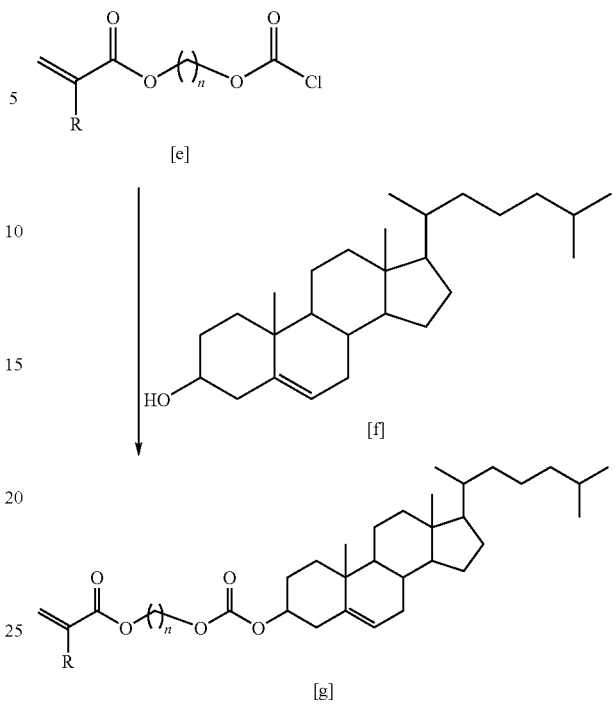

As shown in the synthetic scheme described above, a carbonate derivative [g] can be synthesized by reacting 2-(chlorocarbonyloxy)alkyl acrylate [e] with cholesterol [f].

The compound (10) can be synthesized according to the following synthetic scheme.

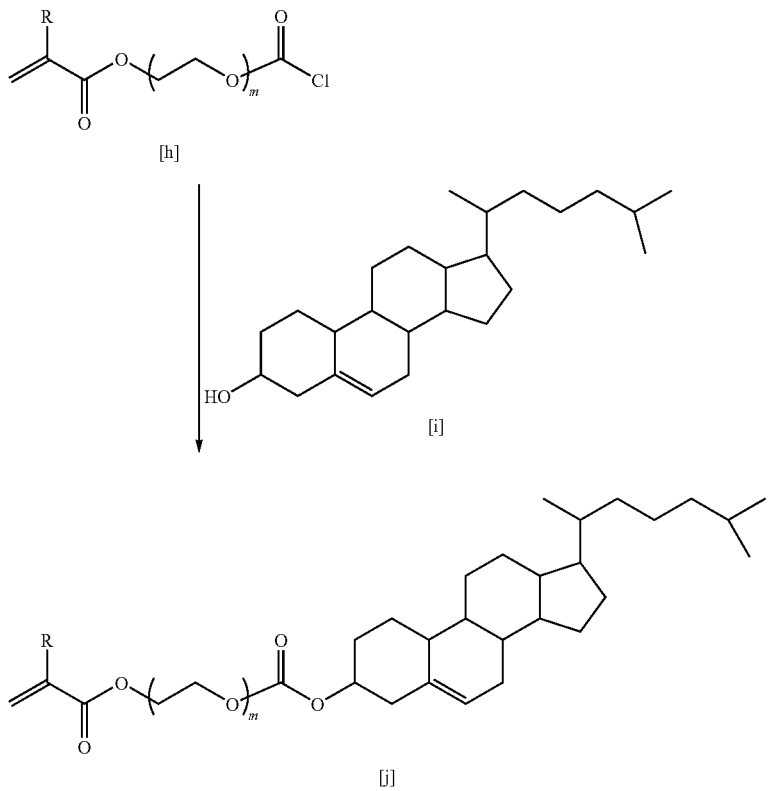

As shown in the synthetic scheme described above, a carbonate derivative [j] can be synthesized by reacting 2-(chlorocarbonyloxy)alkyl ether acrylate [h] with cholesterol [i].

Composition (II)

The composition (II) of the invention includes at least one compound selected from compounds (5) and at least one compound selected from compounds (6). The composition (II) of the invention may further include at least one compound selected from the group of the compound (10) or at least one compound selected from the group of the compound (7) and the compound (8) in addition to the compounds (5) and (6). Further, the composition (II) of the invention may include a polymerizable compound (the other polymerizable compound) other than the compounds (5) to (8) and (10), a non-polymerizable component, an organic solvent and the like.

The preferred embodiment of the composition (II) of the invention includes, for example, the combination of the compound in which r is 5 in Formula (5), the compound in which q is 2 in Formula (6) and the compound in which t is 2 in Formula (10); the combination of the compound in which r is 5 in Formula (5), the compound in which q is 4 in Formula (6) and the compound in which t is 2 in Formula (10); the combination of the compound in which r is 5 in Formula (5), the compound in which q is 2 in Formula (6) and the compound in which t is 3 in Formula (10); the combination of the compound in which r is 5 in Formula (5), the compound in which q is 4 in Formula (6) and the compound in which t is 3 in Formula (10); and the combination of a compound in which r is 5 and R is hydrogen in Formula (5) and a compound in which q is 2 in Formula (6).

The properties of the compounds (5) and (7) and a synthetic method thereof are the same as shown in the compounds (1) to (3) described above, and the properties of the compounds (6) and (8) and a synthetic method thereof are the same as shown in the compound (4) described above.

In the composition (II) of the invention, at least one compound selected from the compounds (5) and at least one compound selected from the compounds (6) as essential components are mixed, and the combination of the structural components, the composition ratio thereof or the temperature in curing is changed, whereby obtained is a composition exhibiting a cholesteric phase in a relatively broad temperature area in the vicinity of room temperature.

In the composition (II) of the invention, a content of the compound (5) is usually approximately 2 to approximately 98 weight %, preferably approximately 50 to approximately 98 weight % and more preferably approximately 60 to approximately 95 weight %, and a content of the compound (6) is usually approximately 2 to approximately 98 weight %, preferably approximately 2 to approximately 50 weight % and more preferably approximately 5 to approximately 40 weight % each based on approximately 100 weight % of the total of the essential components.

At least one selected from the compound (10) or at least one compound selected from the compounds (7) and (8) which is contained in the composition (II) of the invention makes it possible to prevent the composition from being crystallized at room temperature, control a reflected color at a specific temperature and develop a cholesteric phase taking on reflected colors of red, orange, green and blue (purple) in a broader temperature region. Specifically, the compound (10) has a high effect in terms of preventing the composition from being crystallized at room temperature.

In the composition (II) of the invention, a content of the component selected from the compound (10) is preferably approximately 10 to approximately 60 weight %, more preferably approximately 20 to approximately 50 weight % based on approximately 100 weight % of the total of the compounds (5), (6) and (10). Meanwhile, in the composition (II) of the invention, a content of the component selected from the compounds (7) and (8) is preferably approximately 2 to approximately 30 weight %, more preferably approximately 5 to approximately 20 weight % based on approximately 100 weight % of the total of the compounds (5) to (8).

Composition (III)

The composition (III) of the invention includes at least one compound (hereinafter referred to as the "first component") selected from the compounds (9), at least one compound (hereinafter referred to as the "second component") selected from compounds the (8) and at least one compound (hereinafter referred to as the "third component") selected from the group of multifunctional (meth)acrylates and (meth)acryl oligomers.

The composition (III) of the invention may include a polymerizable compound (other polymerizable compound) other than the first component, the second component and the third component each described above, a non-polymerizable component, an organic solvent and the like. The properties of the compound (9) and a synthetic method thereof are the same as shown in the compounds (1) to (3).

In the composition (III) of the invention, the first component, the second component and the third component are mixed, and the combination of the structural components, the composition ratio thereof or the temperature in curing is changed, whereby obtained is a composition exhibiting a cholesteric phase in a relatively broad temperature area in the vicinity of room temperature.

In the composition (III) of the invention, a content of the first component is preferably approximately 50 to approximately 98 weight %, more preferably approximately 60 to approximately 98 weight %; a content of the second component is preferably approximately 2 to approximately 50 weight %, more preferably approximately 2 to approximately 40 weight %; and a content of the third component is preferably approximately 1 to approximately 30 weight %, more preferably approximately 5 to approximately 15 weight % each based on approximately 100 weight % of the total of the essential components.

Composition (IV)

The composition (IV) of the invention includes at least one compound selected from compounds (5) and at least one compound selected from compounds (10). The composition (IV) of the invention may further include at least one compound selected from the group of the compound (4) in addition to the compounds (5) and (10). Further, the composition (IV) of the invention may include a polymerizable compound (the other polymerizable compound) other than the compounds (4), (5) and (10), a non-polymerizable component, an organic solvent and the like.

The preferred embodiment of the composition (IV) of the invention includes, for example, the combination of the compound in which r is 3 in Formula (5) and the compound in which t is 3 in Formula (10); the combination of the compound in which r is 5 in Formula (5) and the compound in which t is 2 in Formula (10); the combination of the compound in which r is 5 in Formula (5) and the compound in which t is 3 in Formula (10); the combination of the compound in which r is 5 in Formula (5) and the compound in which t is 4 in Formula (10); the combination of the compound in which r is 3 in Formula (5), and the compound in which t is 3 in Formula (10) and the compound in which q is 4 in Formula (4); and the combination of the compound in which r is 5 in Formula (5), the compound in which t is 3 and the compound in which q is 2 in Formula (4).

In the composition (IV) of the invention, at least one selected from the compounds (5) and at least one selected from the compounds (10) as essential components are mixed, and the combination of the structural components, the composition ratio thereof or the temperature in curing is changed, whereby obtained is a composition exhibiting a cholesteric phase in a relatively broad temperature area in the vicinity of room temperature.

In the composition (IV) of the invention, a content of the compound (5) is usually approximately 2 to approximately 98 weight %, preferably approximately 50 to approximately 98 weight % and more preferably approximately 60 to approximately 95 weight %, and a content of the compound (10) is usually approximately 2 to approximately 98 weight %, preferably approximately 2 to approximately 50 weight % and more preferably approximately 5 to approximately 40 weight % each based on approximately 100 weight % of the total of the essential components.

At least one compound selected from the compound (4) which is contained in the composition (IV) of the invention makes it possible to control a reflected color at a specific temperature and develop a cholesteric phase taking on reflected colors of red, orange, green and blue (purple) in a broader temperature region.

In the composition (IV) of the invention, a content of the component selected from the compound (4) is preferably approximately 2 to approximately 30 weight %, more preferably approximately 5 to approximately 20 weight % based on approximately 100 weight % of the total of the compounds (4), (5) and (10).

Composition (V)

The composition (V) of the invention includes at least one compound selected from compounds (4) and at least one compound selected from compounds (10). The composition (V) of the invention may include a polymerizable compound (the other polymerizable compound) other than the compounds (4) and (10), a non-polymerizable component, an organic solvent and the like.

The preferred embodiment of the composition (V) of the invention includes, for example, the combination of the compound in which q is 2 in Formula (4) and the compound in which t is 2 in Formula (10); the combination of the compound in which q is 2 in Formula (4) and the compound in which t is 3 in Formula (10); the combination of the compound in which q is 4 in Formula (4) and the compound in which t is 2 in Formula (10); and the combination of the compound in which q is 4 in Formula (4) and the compound in which t is 3 in Formula (10).

In the composition (V) of the invention, at least one compound selected from the compounds (4) and at least one compound selected from the compounds (10) as essential components are mixed, and the combination of the structural components, the composition ratio thereof or the temperature in curing is changed, whereby obtained is a composition exhibiting a cholesteric phase in a relatively broad temperature area in the vicinity of room temperature. Specifically, the compound (10) has a high effect in terms of preventing the composition from being crystallized at room temperature.

In the composition (V) of the invention, a content of the compound (4) is usually approximately 5 to approximately 70 weight %, preferably approximately 20 to approximately 60 weight %, and a content of the compound (10) is usually approximately 30 to approximately 95 weight %, preferably 40 to approximately 80 weight % each based on approximately 100 weight % of the total of the essential components.

At least one compound selected from the compound (4) which is contained in the composition (IV) of the invention makes it possible to control a reflected color at a specific temperature and develop a cholesteric phase taking on reflected colors of red, orange, green and blue (purple) in a broader temperature region.

In the composition (IV) of the invention, a content of the component selected from the compound (4) is preferably approximately 2 to approximately 30 weight %, more preferably approximately 5 to approximately 20 weight % based on approximately 100 weight % of the total of the compounds (4), (5) and (10).

Other Polymerizable Compound

The polymerizable liquid crystal composition of the invention may contain the other polymerizable compound as long as the effects of the invention are not damaged. The other polymerizable compound may be liquid crystalline or non-liquid crystalline.

Publicly known polymerizable liquid crystal compounds can be used for the other polymerizable compound having a liquid crystallinity and include the following compounds.

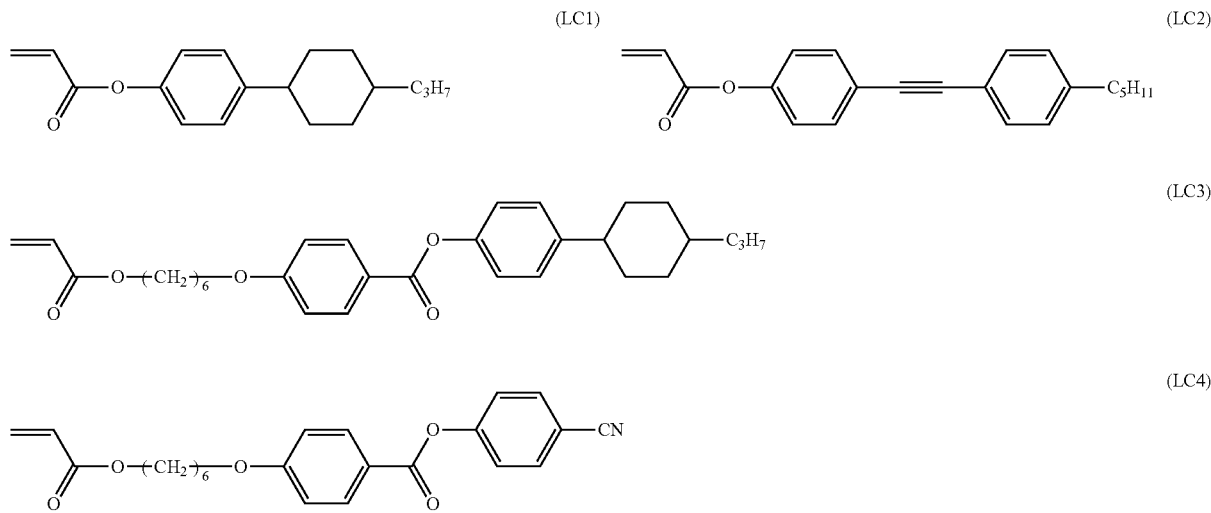

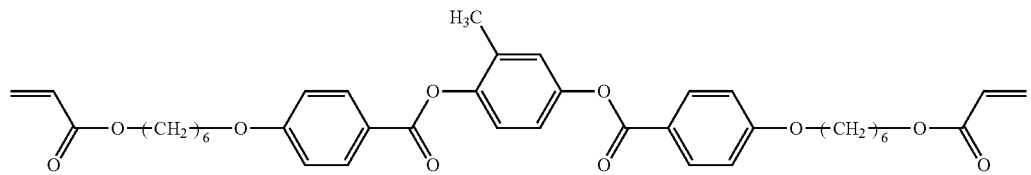
(LC5)

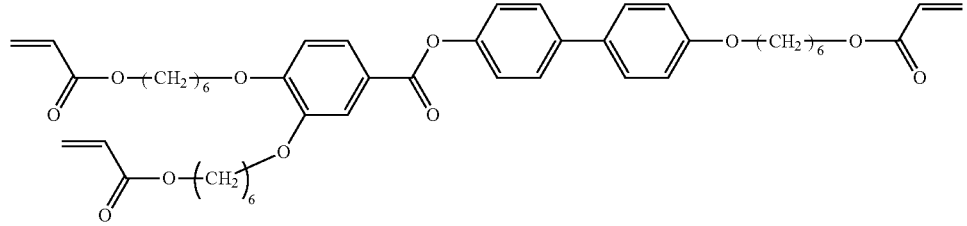
(LC6)

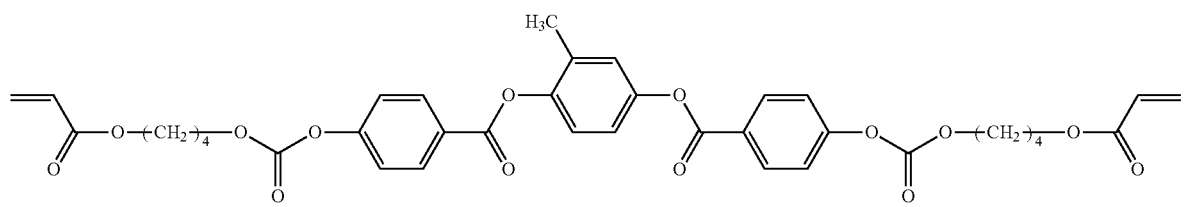
(LC7)

The other polymerizable compounds having a liquid crystallinity may be used alone or in combination of two or more kinds thereof. A content of the other polymerizable compounds having a liquid crystallinity in the composition of the invention is preferably approximately 2 to approximately 30 weight %, more preferably approximately 2 to approximately 15 weight % based on approximately 100 weight % of the total of the essential components. A content of the other polymerizable compounds having a liquid crystallinity which falls in the range described above makes it possible to control temperature at which a cholesteric phase is developed to room temperature or higher.

A system used as a binder for a coating material can be used for the other polymerizable compound having a non-liquid crystallinity. The above binder includes monomer agents, polymer binders and mixtures thereof.

The monomer agents are compounds having a polymerizable group (hereinafter referred to as a "cross-linkable group"). The cross-linkable group includes, for example, acryl, methacryl, α-halogenated acryl, vinyl, vinyl ether, oxirane, oxetane, cyanate and isocyanate groups. Among them, acryl, methacryl and vinyl ether groups are preferred. The monomer agents may be compounds having one cross-linkable group or compounds having plural cross-linkable groups.

The monomer agent having one cross-linkable group includes, for example, methyl acrylate, ethyl acrylate, butyl acrylate, isobutyl acrylate, 2-ethylhexyl acrylate, methyl methacrylate, butyl methacrylate, lauryl methacrylate, styrene, acrylonitrile, acrylamide, N-methylolacrylamide, β-hydroxyethyl methacrylate, glycidyl methacrylate, acrylic acid, methacrylic acid, itaconic acid, maleic anhydride and aginidinyl methacrylate.

The monomer agent having two cross-linkable groups includes, for example, diacrylates, divinyl ethers and dimethacrylates of propanediol, butanediol, hexanediol, ethylene glycol, diethylene glycol, triethylene glycol or tetrapropylene glycol.

The monomer agent having three cross-linkable groups includes, for example, triacrylates, trivinyl ethers and trimethacrylates of trimethylolpropane, ethoxylated trimethylolpropane having approximately 1 to approximately 20 ethylene oxide structural units, propoxylated trimethylolpropane having approximately 1 to approximately 20 propylene oxide structural units or ethoxylated.propoxylated trimethylolpropane having approximately 1 to approximately 20 ethylene oxide structural units and propylene oxide structural units in total; and triacrylates, trivinyl ethers and trimethacrylates of ethoxylated glycerin having approximately 1 to approximately 20 ethylene oxide structural units or propoxylated glycerin having approximately 1 to approximately 20 propylene oxide structural units, such as glycerin epoxy triacrylate.

The monomer agent having four cross-linkable groups includes, for example, pentaerythritol tetraacrylate, and tetraacrylates, tetravinyl ethers and tetramethacrylates of ethoxylated bis-tetramethylolpropane having approximately 1 to approximately 20 ethylene oxide structural units, propoxylated bis-trimethylolpropane having approximately 1 to approximately 20 propylene oxide structural units or ethoxylated.propoxylated bistrimethylolpropane having approximately 1 to approximately 20 ethylene oxide structural units and propylene oxide structural units in total.

The monomer agent having five cross-linkable groups includes, for example, dipentaerythritol pentaacrylate, ethoxylated dipentaerythritol pentaacrylate having approximately 1 to approximately 20 ethylene oxide structural units, propoxylated dipentaerythritol pentaacrylate having approximately 1 to approximately 20 propylene oxide structural units, and pentaacrylates, pentavinyl ethers and pentatrimethacrylates of ethoxylated.propoxylated dipentaerythritol having approximately 1 to approximately 20 ethylene oxide structural units and propylene oxide structural units in total.

The polymer binder described above includes (meth)acryl oligomers, urethane acrylate oligomers, epoxy oligomers and the like.

The other polymerizable compounds having a non-liquid crystallinity are more preferably monofunctional (meth)acrylate monomers, multifunctional (meth)acrylate monomers and (meth)acryl oligomers. The multifunctional (meth)acrylate monomers and the (meth)acryl oligomers can be used as the third component in the composition (III) of the invention, and in this case, they are not included in the other polymerizable compounds.

The other polymerizable compounds having a non-liquid crystallinity may be used alone or in combination of two or more kinds thereof. In the composition of the invention, a content of the other polymerizable compounds having a non-liquid crystallinity is different depending on the structure of the polymerizable liquid crystal compound and the composition ratio thereof, and it is preferably approximately 40 weight % or less, more preferably approximately 30 weight % or less and further preferably approximately 20 weight % or less based on approximately 100 weight % of the total of the essential components. A content of the other polymerizable compounds having a non-liquid crystallinity which falls in the range described above maintains a liquid crystal phase of the composition without bringing about phase separation.

Non-Polymerizable Component

The polymerizable liquid crystal composition of the invention may be blended with a non-polymerizable component as long as the effects of the invention are not damaged. The non-polymerizable component may be liquid crystalline or non-liquid crystalline and includes, for example, non-polymerizable liquid crystal compounds, extender pigments, colorants, dispersants, polymerization initiators, sensitizers, polymerization inhibitors, oxygen inhibitors, antioxidants, UV absorbers, surfactants, adhesive aids, adhesion accelerators, storage stabilizers, defoamers, flocculation preventives and the like.

The non-polymerizable liquid crystal compounds are described in LiqCryst, LCI Publisher GmbH, Hamburg, Germany which is a data base for liquid crystal compounds. The non-polymerizable liquid crystal compounds may be used alone or in combination of two or more kinds thereof.

The extender pigments which are generally added to coating materials include, for example, barium sulfate, barium carbonate, calcium carbonate, magnesium carbonate, silica, titanium oxide, mica, sericite, talc and the like. The above extender pigments may be used alone or in combination of two or more kinds thereof.

The colorants include organic pigments which are generally added to resins, and they include, to be more specific, soluble azo, insoluble azo, polyazo, phthalocyanine, anthraquinone, thioindigo, perylene, perinone, dioxazine, quinacridone, isoindolinone, quinophthalone, diketopyrrolopyrrole, anthraquinone, perinone, quinophthalone, azo, carbon black and the like. Among them, soluble azo, insoluble azo, polyazo, phthalocyanine, quinacridone, dioxazine, quinophthalone and carbon black are preferred.

Low molecular or high molecular dispersants which are conventionally used can be used for the dispersants. The low molecular dispersants include, for example, stearic acid and the like, and the high molecular dispersants include polyurethanes having a sulfonate group, a phosphate group, a phosphonate group or a carboxyl group, carboxyl group—containing vinyl chloride polymers, polyiminepolyesters, polyether acrylate and the like.

The polymerizable liquid crystal composition of the invention may contain a conventional photopolymerization initiator when subjected to optical radical polymerization. The initiator has a maximum absorption wavelength in an ultraviolet, near ultraviolet or visible light region, and a polymer may be produced by irradiating the composition therewith at room temperature or heating at the same time as irradiation.

The photopolymerization initiators include, for example, 2,2-dimethoxy-1,2-diphenylethane-1-one (Irgacure 651™), 1-hydroxycyclohexyl phenyl ketone (Irgacure 184™), 2-hydroxy-2-methyl-1-phenyl-propane-1-one (Dalocure 1173™, Irgacure 500™, Irgacure 1000™, 1-[4-(2-hydroxyethoxy)-phenyl]-2-hydroxy-2-methyl-1-propane-1-one (Irgacure 295™), 2-methyl-1-[4-(methylthio)phenyl]-2-morpholinopropane-1-one (Irgacure 907™), 2-benzyl-2-dimethylamino-1-(4-morpholinophenyl)-butanone-1 (Irgacure 369™), 2-(dimethylamino)-2-[(4-methylphenyl)methyl]-1-[4-(4-morpholinyl)phenyl]-1-butanone (Irgacure 379™), Irgacure 1800™, Irgacure 1850™, Dalocure 4265™, Dalocure 1116™, Irgacure 784™, bis(2,4,6-trimethylbenzoyl)-phenylphosphine oxide (Irgacure 819™), Irgacure 784™, 1,2-octanedione-1-[4-(phenylthio)-2-(O-benzoyloxime)] (IrgacureOXE01™), ethanone-1-[9-ethyl-6-(2-methylbenzoyl)-9H-carbazole-3-yl]-1-(O-acetyl oxime) (Irgacure OXE02™), 2-hydroxy-1-[4-[4-(2-hydroxy-2-methylpropionyl)-benzyl]phenyl]-2-methyl-propane-1-one (Irgacure 127™) and Irgacure 754™ which are products manufactured by Ciba Specialty Chemicals K. K.

The photopolymerization initiators include, in addition to the above compounds, acetophenone, benzophenone, 4,4'-bisdimethylaminobenzophenone, 3,3-dimethyl-4-methoxybenzophenone, benzil, benzoyl, benzoin ethyl ether, benzoin butyl ether, benzoin isobutyl ether, azoisobutylnitrile, 2-chlorothioxanthone, 2,4-dimethylthioxanthone, 2,4-diisopropylthioxanthone, 2-isopropylthioxanthone, 2,4-diethylthioxanthone, methylphenyl glyoxylate, 3,3',4,4-tetra(t-butylperoxycarbonyl)benzophenone, ethyl p-dimethylaminobenzoate, 2-dimethylaminoeklbenzoate, isoamyl p-dimethylaminobenzoate, N,N-dimethylaminoethyl methacrylate, a benzophenone/methyltriethanolamine mixture, a 2,2-diethylxanthone/methyl p-dimethylaminobenzoate mixture, 2-methyl-1-[4-(methylthio)phenyl]-2-morpholinopropane-1-one, benzyl dimethyl ketal, acetophenone dimethyl ketal, 2,2-dimethoxy-2-phenylacetophenone, 2,2-diethoxy-2-phenylacetophenone, 1,1-dichloroacetophenone, diethoxyacetophenone, 2-hydroxy-2-methyl-phenylpropane-1-one, 1-hydroxycyclohexyl phenyl ketone, 2-ethylanthraquinone, 2-tertiary butylanthraquinone, 2-chloroanthraquinone, 2-aminoanthraquinone, benzophenone, 4-benzoyl-4'-methyldiphenyl sulfide, 4,4'-bismethylaminobenzophenone, 2,4,6-trimethylbenzoyldiphenylphosphine oxide, bis(2,4,6-trimethylbenzoyl)-phenylphosphine oxide and the like.

The polymerization initiators are preferably used in an amount falling in a range of approximately 0.01 to approximately 10 parts by weight per approximately 100 parts by weight of the total amount of the compounds having an ethylenically unsaturated bond which is radically polymerizable.

The composition of the invention may contain a sensitizer in addition to the polymerization initiator. The sensitizer includes, for example, coumarins having substituents at a 3-position and/or a 7-position, flavones, dibenzalacetones, dibenzalcyclohexanes, chalcones, xanthenes, thioxanthenes, porphyrins, acridines and the like.

The composition of the invention may contain a surfactant such as a nonionic surfactant, a cationic surfactant, an anionic surfactant and the like in order to enhance a coating property on an objective substrate. It includes, to be specific: nonionic surfactants including polyoxyethylene alkyl ethers such as polyoxyethylene lauryl ether, polyoxyethylene stearyl ether and polyoxyethylene oleyl ether, polyoxyethylene aryl ethers such as polyoxyethylene octylphenyl ether and polyoxyethylene nonylphenyl ether and polyethylene glycol dialkyl esters such as polyethylene glycol dilaurate and polyethylene glycol distearate; fluorine base surfactants such as Eftop EF301™, Eftop EF303™ and Eftop EF352™ (manufactured by Shin Akita Chemical Co., Ltd.), Megafac F171™, Megafac F172™ and Megafac F173™ (manufactured by Dainippon Ink & Chemicals Inc.), Fluorad FC430™ and Fluorad FC431™ (manufactured by Sumitomo 3M Limited) and Asahi Guard AG710™, Surflon S-382™, Surflon SC-101™, Surflon SC-102™, Surflon SC-103™, Surflon SC-104™, Surflon SC-105™ and Surflon SC-106™ (manufactured by Asahi Glass Co., Ltd.); Organosiloxane Polymer KP341™ (manufactured by Shin-Etsu Chemical Co., Ltd.) and acrylic acid base or methacrylic acid base (co)polymer Polyflow No. 57™ and Polyflow No. 95™ (manufactured by Kyoeisha Chemical Co., Ltd.). The surfactants are used in an amount of approximately 5 parts by weight or less based on the polymer.

The polymerizable liquid crystal composition of the invention may contain a close adhesiveness-accelerating agent in order to improve a close adhesiveness on a substrate which is an object for applying. The close adhesiveness-accelerating agent includes, for example, vinyltrimethoxysilane, vinyltriethoxysilane, vinyltris(2-methoxyethoxy)silane, N-(2-aminoethyl)-3-aminopropyltrimethoxysilane, 3-aminopropyltrimethoxysilane, 3-glycidoxypropyltrimethoxysilane, 3-glycidoxypropyldimethoxysilane, 3-glycidoxypropylmethyldimethoxysilane, 2-(3,4-epoxycyclohexyl)ethyltimethoxysilane, 3-chloropropylmethyldimethoxysilane, 3-chloropropyltrimethoxysilane, 3-methacryloxypropyltrimethoxysilane, 3-mercaptopropyltrimethoxysilane and the like.

The antioxidants include, for example, 2,2-methylenebis (4-methyl-6-t-butylphenol), 2,6-di-t-butyl-4-methylphenol (BHT) and the like.

The UV absorbers include, for example, 2-(3-t-butyl-5-methyl-2-hydroxyphenyl)-5-chlorobenzotriazole, alkoxybenzophenones and the like.

The flocculation preventives include, for example, sodium polyacrylate and the like.

Organic Solvent

The polymerizable liquid crystal composition of the invention may contain an organic solvent in order to dilute the composition or enhance the coating property. The organic solvent includes linear or branched esters, particularly acetic esters, cyclic ethers, cyclic esters, alcohols, lactone, aliphatic hydrocarbons, aromatic hydrocarbons, toluene, xylene, cyclohexane, ketones, amides, N-alkylpyrrolidones, tetrahydrofuran, dioxane, methyl ethyl ketone and the like. The organic solvents may be used alone or in combination of two or more kinds thereof.

Polymer

The polymer according to the invention is obtained by polymerizing the polymerizable liquid crystal composition of the invention, and a cholesteric liquid crystal phase of the composition is fixed to reflect light of a wavelength according to the desired colors and the purposes. The polymerization reaction of the composition may be either thermal polymerization by heating or photopolymerization by irradiation with light, and it may be carried out by a method obtained by combining both.

The kind of preferred light used for photopolymerization is a UV ray, a visible light and an infrared ray, and an electromagnetic wave such as an electron beam and an X-ray may be used. Usually, a UV ray or a visible light is used. The range of the wavelength is approximately 150 to approximately 500 nm, preferably approximately 250 to approximately 450 nm and particularly preferably approximately 300 to approximately 400 nm. The light source includes a low pressure mercury lamp (a bactericidal lamp, a fluorescent chemical lamp and a black light), a high pressure discharge lamp (a high pressure mercury lamp and a metal halide lamp) and a short arc discharge lamp (an extra-high pressure mercury lamp, a xenon lamp and a mercury xenon lamp), and an extra-high pressure mercury lamp is preferred.

Light coming from the light source may be irradiated on the composition as it is, or a specific wavelength (or a specific wavelength region) which is selected through a filter may be irradiated on the composition. The irradiation energy density falls in the range of approximately 2 to approximately 5,000 mJ/cm$^2$, preferably approximately 10 to approximately 3,000 mJ/cm$^2$ and particularly preferably approximately 100 to approximately 2,000 mJ/cm$^2$. The illuminance falls in a range of approximately 0.1 to approximately 5000 mW/cm$^2$, preferably approximately 1 to approximately 2,000 mW/cm$^2$.

The polymer of the invention can be obtained by applying the polymerizable liquid crystal composition of the invention directly on the surface of a substrate which is an object and then polymerizing it. Accordingly, multistage operation in which a cholesteric polymer is crushed into a flake form or in which cholesteric liquid crystal is microencapsulated, mixed again with a solvent and the like and applied on an object does not have to be carried out. The form of the polymer shall not specifically be restricted and may be a film form, a plate and the like, and the polymer may be molded.

In the composition of the invention, a wavelength region of light reflected by a cholesteric phase can be controlled in a wide range of red, green, blue and purple by changing the combination of the structural components, the composition ratio thereof and a curing temperature of the composition. Accordingly, the polymer reflecting light of a wavelength according to the desired colors and the purposes can be obtained without strictly controlling the temperature condition in curing.

Uses

Uses for the polymerizable liquid crystal composition, for example, cosmetic ingredients, printing inks, UV curing type printing inks and the like.

Uses for the polymer of the invention include conventional films, cosmetic ingredients, color materials, for example, liquid crystal pigments, coating materials, spray inks, print inks and the like. Further, it can be used as well for cosmetics (for example, lip rouge, lip cream, lip gloss, eye shadow, eye liner, mascara, rouge, liquid foundation and nail colors), printed matters for preventing counterfeit, ornamental articles, toys or optical films such as polarizing plates, compensation plates and color filters in optical elements such as liquid crystal displays and holographic devices.

The objects, features, advantages and ideas of the invention will be apparent to those skilled in the art from the description provided in the specification, and the invention will be readily practicable by those skilled in the art on the basis of the description appearing herein. The Description of the Preferred Embodiments and the Examples which show preferred modes for practicing the invention are included for the purpose of illustration and explanation, and are not intended to limit the scope of the claims. It will be apparent to those skilled in the art that various modifications may be made in how the invention is practiced based on described aspects in the specification without departing from the spirit and scope of the invention disclosed herein. Thus, it is intended that the invention covers the modifications and variations of this invention that come within the scope of any claims and their equivalents.

EXAMPLES

The present invention shall more specifically be explained below with reference to examples, but the present invention shall not be restricted to these examples.

Synthetic Example 1

A compound (compound in which m is 5 in Formula (1)) represented by the following formula was synthesized in the following manner.

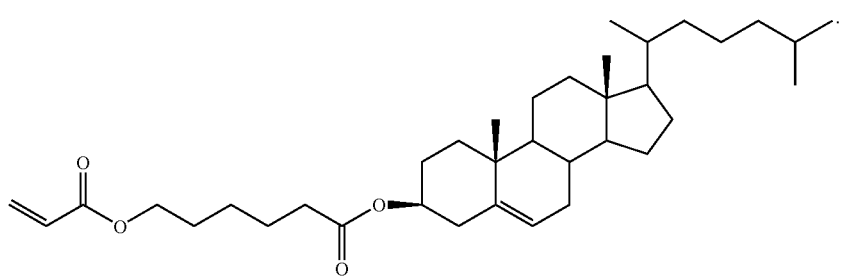

First Step:

Sodium hydroxide 173 g was dissolved in 867 g of water, and then 150 g of ε-caprolactone which was a raw material was added dropwise thereto and stirred at room temperature for 5 hours. After neutralized with 6N hydrochloric acid, the solution was extracted with ethyl acetate, and then the organic layer was washed with water. The organic layer was dried on anhydrous magnesium sulfate, and then the solvent was distilled off under reduced pressure. The residue was recrystallized from a mixed solvent of tetrahydrofuran (THF) and heptane to obtain 106.47 g of 1-hydroxyhexanoic acid. $^1$H-NMR (CDCl$_3$; δ ppm): 3.68 (t, 2H), 2.38 (t, 2H), 1.57 to 1.72 (m, 4H), 1.39 to 1.47 (m, 2H).

Second Step:

Acrylic chloride 80 g was dropwise added to a mixture of 1067 g of 1-hydroxyhexanoic acid, 109 g of N,N-dimethylaniline, 0.9 g of BHT and 1,000 mL of dioxane at room temperature, and subsequently the solution was stirred at 60° C. for 2 hours. The reaction mixture was poured into ice and water, and ethyl acetate was added thereto and stirred. After separating the liquid, the ethyl acetate layer was washed in the order of 1N hydrochloric acid, a saturated sodium carbonate aqueous solution and water and dried on anhydrous magnesium sulfate, and then the solvent was distilled off under reduced pressure to obtain a concentrate (148.56 g) of 6-acryloyloxyhexanoic acid. $^1$H-NMR (CDCl$_3$; δ ppm): 6.38 (dd, 1H), 6.14 (dd, 1H), 5.83 (dd, 1H), 4.16 (t, 2H), 2.38 (t, 2H), 1.64 to 1.73 (m, 4H), 1.40 to 1.47 (m, 2H).

Third Step:

A dichloromethane 80 mL solution of 19 g of N,N'-dicyclohexylcarbodiimide was dropwise added to a mixture of 70 g of 6-acryloyloxyhexanoic acid, 121 g of cholesterol, 19 g of 4-dimethylaminopyridine and 1,500 mL of dichloromethane under cooling with ice. The solution was stirred at room temperature for 18 hours, and insoluble matters were removed by filtering. Water was added to the filtrate, and the organic layer was washed in the order of 1N hydrochloric acid, a 2N sodium hydroxide aqueous solution and water and dried on anhydrous magnesium sulfate. Then, the solvent was distilled off under reduced pressure. The residue was filtered through celite, and the filtrate was separated by silica gel chromatography (heptane/ethyl acetate=9/1) and then recrystallized from a mixed solvent of diethyl ether and ethanol to obtain 100.35 g of 6-acryloyloxyhexanoic acid cholesterol ester. Melting point: 45.3 to 45.8° C. $^1$H-NMR (CDCl$_3$; δ ppm): 6.41 (dd, 1H), 6.12 (dd, 1H), 5.37 (d, 1H), 4.59 to 4.63 (m, 1H), 4.15 (t, 2H), 2.29 (t, 2H), 0.6 to 1.96 (m, 47H).

Among compounds used in the following examples, the compounds represented by Formulas (1) to (3), (5), (7) and (9) were synthesized by the same method as described above.

Example A1

Prepared was a composition comprising 91% by weight of the compound (compound in which m is 5 in Formula (1)) obtained in Synthetic Example 1 and 9% by weight of a compound in which n is 3 and R is hydrogen in Formula (2). The composition showed selective reflection of a green color at 22° C. The composition (1 g) was mixed with 0.01 g of Irgacure 651™ (manufactured by Ciba Specialty Chemicals K. K.) as a polymerization initiator, and the mixture was dissolved in toluene and applied on a glass substrate. After applied, the substrate was subjected to heat treatment for 3 minutes in an oven set to 120° C. to remove the solvent, whereby a coating film was formed. Then, the coating film was irradiated with a UV ray for 30 seconds by means of a high pressure mercury lamp (70 mW/cm$^2$). The above composition was polymerized by irradiation and showed the same selective reflection of a green color as in applying the composition before polymerized on a glass substrate. The results thereof are shown in Table 1.

Examples A2 to A8

Polymers were produced in the same manner as in Example A1 to observe reflected colors, except that compositions having formulations shown in Table 1 were prepared. The results thereof are shown in Table 1.

TABLE 1

| | Compound (1) m = 5 % by weight | Compound (2) n = 3, R=H % by weight | Reflected Color 22° C. | 40° C. |
|---|---|---|---|---|
| Example A1 | 91 | 9 | Green | |
| Example A2 | 83 | 17 | Green | |
| Example A3 | 80 | 20 | Green | |
| Example A4 | 70 | 30 | Greenish yellow | |
| Example A5 | 67 | 33 | Orange + green | Viridian |
| Example A6 | 62 | 38 | Orange (vermilion) | Green |
| Example A7 | 57 | 43 | Sanguine | Greenish yellow |
| Example A8 | 50 | 50 | Ruby red | Greenish yellow |

Examples B1 to B4

Polymers were produced in the same manner as in Example A1 to observe reflected colors, except that compositions having formulations shown in Table 2 were prepared. The results thereof are shown in Table 2.

Example C1

A polymer was produced in the same manner as in Example A1 to observe a reflected color, except that a composition having a formulation shown in Table 2 was prepared. The results thereof are shown in Table 2.

TABLE 2

| | Compound (1) m = 5 % by weight | Compound (1) m = 10 % by weight | Compound (2) n = 3 R=H % by weight | Compound (4) q = 2 R=H % by weight | Reflected Color 22° C. | 40° C. |
|---|---|---|---|---|---|---|
| Ex. B1 | 44 | 11 | 44 | — | Red | Green |
| Ex. B2 | 40 | 20 | 40 | — | Orange | Viridian |
| Ex. B3 | 36 | 27 | 36 | — | Green | Blue |
| Ex. B4 | 33 | 33 | 33 | — | Blue | Blue |
| Ex. C1 | 44 | — | 44 | 12 | Transparent (red) | |

Examples D1 to D5

Polymers were produced in the same manner as in Example A1 to observe reflected colors, except that compositions shown in Table 3 were prepared. The results thereof are shown in Table 3.

TABLE 3

| | Compound (5) r = 5 R=H % by weight | Compound (6) q = 2 % by weight | Reflected Color 22° C. | 40° C. |
|---|---|---|---|---|
| Ex. D1 | 5 | 95 | Red to orange | |
| Ex. D2 | 10 | 90 | Greenish yellow | |
| Ex. D3 | 20 | 80 | Green | |
| Ex. D4 | 30 | 70 | Blue | Blue |
| Ex. D5 | 40 | 60 | Blue | Blue |

Reference Example E1 and Example E2

Polymers were produced in the same manner as in Example A1 to observe reflected colors, except that compositions shown in Table 4 were prepared. The results thereof are shown in Table 4. Trimethylolpropane triacrylate was used as the third component.

TABLE 4

| | First Component Compound (9) s = 5, R=H % by weight | Second Component Compound (8) q = 2 % by weight | Third Component % by weight | Reflected Color 25° C. | 35° C. |
|---|---|---|---|---|---|
| Reference Example E1 | 60 | 40 | — | Colorless | Red |
| Example E2 | 55 | 36 | 9 | Red | Red |

Examples F1 to F13

Polymers were produced in the same manner as in Example A1 to observe reflected colors, except that compositions shown in Table 5 were prepared. The results thereof are shown in Table 5.

As shown in Table 6, temperature dependency of reflected colors in the cholesteric reflection bands of the compositions comprising the same monofunctional acrylates as the compounds of the present invention is shown in Comparative Examples 1 to 7. It can be found that particularly in Comparative Example 1, a cholesteric phase taking on reflected colors of red to purple is maintained in a broad temperature range of −15 to 68° C.

TABLE 5

|  | Compound (5) | | Compound (4) | | Compound (10) | Reflected Color | |
|---|---|---|---|---|---|---|---|
|  | r = 3, R=H | r = 5, R=H | q = 2, R=H | q = 4, R=H | t = 3, R=H |  |  |
|  | % by weight | % by weight | % by weight | % by weight | % by weight | 24° C. | 40° C. |
| Ex. F1 |  | 33 | 33 |  | 33 | Orange to greenish yellow | Green |
| Ex. F2 |  | 38 | 38 |  | 24 | Red | Red |
| Ex. F3 | 33 | 33 |  |  | 33 | Orange to greenish yellow | Green |
| Ex. F4 | 38 | 38 |  |  | 24 | Vermilion | Greenish yellow |
| Ex. F5 | 43 | 43 |  |  | 14 | Red | Green |
| Ex. F6 | 44 | 44 |  |  | 12 | Red | Greenish yellow |
| Ex. F7 |  | 33 | 33 |  | 33 | Blue | Blue |
| Ex. F8 | 25 | 25 |  |  | 50 | Orange to greenish yellow | Greenish yellow |
| Ex. F9 | 25 | 50 |  |  | 25 | Red | Red |
| Ex. F10 | 25 | 50 |  |  | 25 | Green | Green |
| Ex. F11 |  | 50 |  |  | 50 | Blue | Blue |
| Ex. F12 |  |  | 20 | 40 | 40 | Red | Orange |
| Ex. F13 |  |  |  | 50 | 50 | Blue | Blue |

Comparative Examples 1 to 11

Results obtained in examples described in JP S59-109505 A/1984 shall be shown as comparative examples in Table 6.

TABLE 6

|  | Compound (1) | Compound (2) | | Compound (3) | Compound (4) | | | Reflected |  |
|---|---|---|---|---|---|---|---|---|---|
|  |  | n = 3 | n = 3 |  | q = 2 | q = 6 | q = 2 |  |  |
|  | m = 5 | m = 10 | R=H | R=CH₃ | p = 5 | p = 10 | R=H | R=H | R=CH₃ | Color | Remarks |
| Comp. Ex. 1 | — | 50 | 50 | — | — | — | — | — | — | Purple to orange red | 68 to −15° C. |
| Comp. Ex. 2 | — | — | — | — | 50 | 50 | — | — | — | Green to orange | 475 to −15° C. |
| Comp. Ex. 3 | — | — | 50 | — | 50 | — | — | — | — | Purple to red | 50 to −5° C. |
| Comp. Ex. 4 | — | — | — | 50 | — | 50 | — | — | — | Bluish purple to red | 40 to −5° C. |
| Comp. Ex. 5 | — | — | — | 50 | 50 | — | — | — | — | Green to red | 45 to 30° C. |
| Comp. Ex. 6 | — | — | — | — | — | 50 | 50 | — | — | Orange green to red | 32 to 0° C. |
| Comp. Ex. 7 | — | — | 30 | — | 40 | 20 | — | — | — | Purple to orange | 16 to 6° C. |
| Comp. Ex. 8 | — | — | — | — | — | 50 | — | — | 50 | | 585 nm (25.5° C.) |
| Comp. Ex. 9 | 75 | — | — | — | — | — | 25 | — | — | | 563 nm (25.5° C.) |
| Comp. Ex. 10 | 50 | — | — | — | — | 50 | — | — | — | | 950 nm (24.5° C.) |
| Comp. Ex. 11 | 50 | — | — | — | — | — | 50 | — | — | | 1260 nm (25.5° C.) |

However, the reflected colors shown in the vicinity of room temperature are limited. That is, a film having an inherent reflected color which was produced by using the composition prepared in Comparative Example 1 was prepared as well, and the temperature of the composition was changed at the intervals of 10° C., 18° C., 23° C. and 32° C. to control the reflected colors. Thus, it is not described in JP S59-109505 A/1984 that a polymer taking on the specific reflected colors of red, green and blue at a fixed temperature of room temperature is obtained as is the case with the invention.

Also, in other Comparative Examples 2, 3, 4 and 6, red and orange colors were shown at a relatively low temperature, that is, room temperature or lower. In Comparative Examples 5 and 7, a temperature range in a cholesteric phase area fallen in a range of 10 to 15° C. It can not be found that stable reflected colors of red to blue (purple) are shown at room temperature in all the above comparative examples. The invention is characterized by providing a polymerizable liquid crystal composition showing a reflected color in a broad range of red to blue (purple) at some fixed room temperature by changing the constitution of the composition and providing a polymer thereof.

In Comparative Example 10, the composition having a component ratio of 1:1 didn't take on a reflected color in the vicinity of room temperature. Compositions in which a composition ratio was changed as is the case with Example 9 showed inherent reflected colors at room temperature. However, polymerizable liquid crystal compositions showing reflected colors in a broad range of red to blue (purple) in the vicinity of room temperature are not obtained from only the above two component system.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A polymerizable liquid crystal composition comprising at least one compound selected from the group of compounds represented by Formula (5) and at least one compound selected from the group of compounds represented by Formula (6):

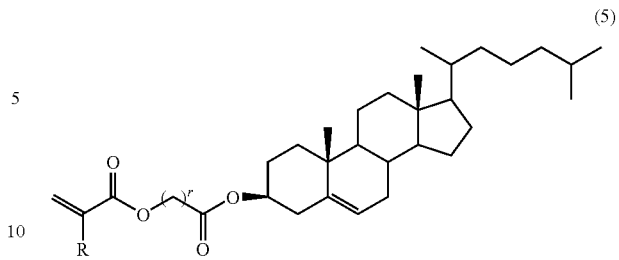

wherein r is an integer of 3 to 9, and R is hydrogen or methyl; and

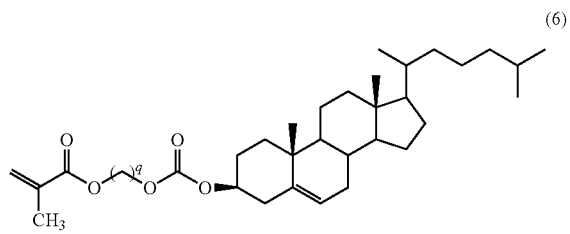

wherein q is 2, 4 or 6.

2. The polymerizable liquid crystal composition of claim 1, further comprising at least one compound selected from the group of compounds represented by Formula (10):

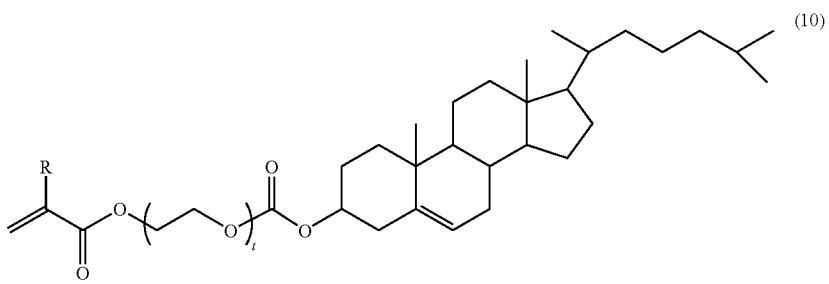

wherein t is 2, 3 or 4, and R is hydrogen or methyl.

3. The polymerizable liquid crystal composition of claim 2, comprising the compound in which r is 5 in Formula (5), the compound in which q is 2 in Formula (6) and the compound in which t is 2 in Formula (10).

4. The polymerizable liquid crystal composition of claim 2, comprising the compound in which r is 5 in Formula (5), the compound in which q is 4 in Formula (6) and the compound in which t is 2 in Formula (10).

5. The polymerizable liquid crystal composition of claim 2, comprising the compound in which r is 5 in Formula (5), the compound in which q is 2 in Formula (6) and the compound in which t is 3 in Formula (10).

6. The polymerizable liquid crystal composition of claim 2, comprising the compound in which r is 5 in Formula (5), the compound in which q is 4 in Formula (6) and the compound in which t is 3 in Formula (10).

7. The polymerizable liquid crystal composition of claim 1, further comprising at least one compound selected from the group of compounds represented by Formulas (7) and (8):

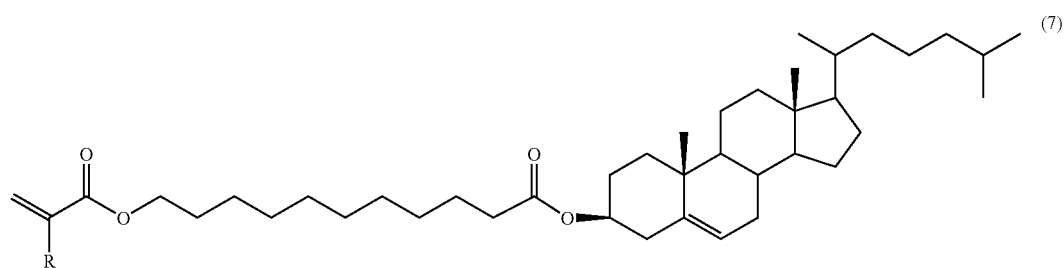

(7)

wherein R is hydrogen or methyl; and

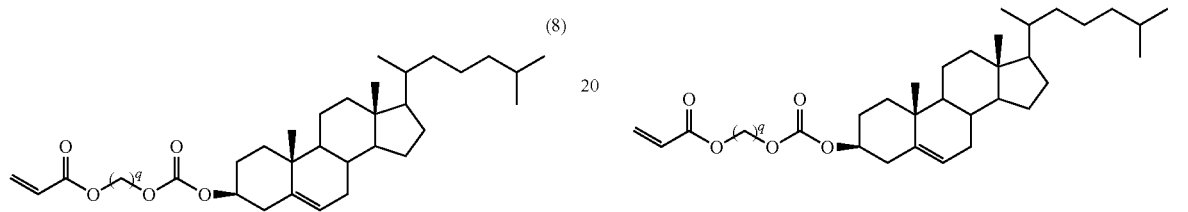

(8)

wherein q is 2, 4 or 6.

8. The polymerizable liquid crystal composition of claim 1, comprising the compound in which r is 5 and R is hydrogen in Formula (5) and the compound in which q is 2 in Formula (6).

9. A polymerizable liquid crystal composition comprising at least one compound selected from the group of compounds represented by Formula (9),

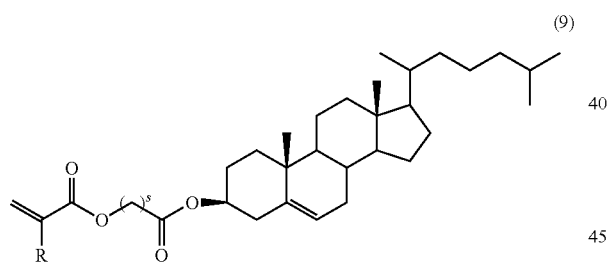

(9)

wherein s is an integer of 3 to 10, and R is hydrogen or methyl;

at least one compound selected from the group of compounds represented by Formula (8)

wherein q is 2, 4 or 6; and at least one compound selected from the group of multi-functional (meth)acryl monomers and (meth)acryl oligomers.

10. A polymerizable liquid crystal composition comprising at least one compound selected from the group of compounds represented by Formula (5) and at least one compound selected from the group of compounds represented by Formula (10):

(5)

wherein r is an integer of 3 to 9, and R is hydrogen or methyl; and

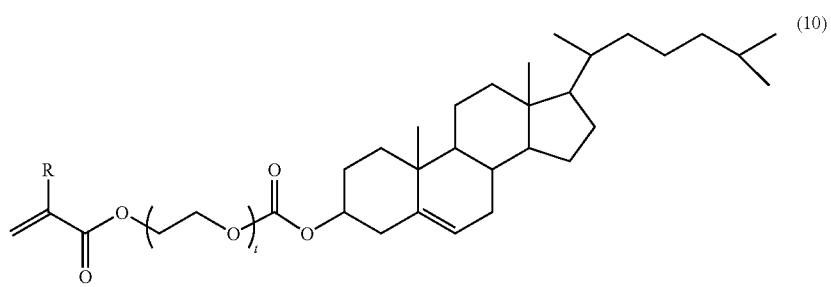

(10)

wherein t is 2, 3 or 4, and R is hydrogen or methyl.

11. The polymerizable liquid crystal composition of claim 10, comprising the compound in which r is 3 in Formula (5) and the compound in which t is 3 in Formula (10).

12. The polymerizable liquid crystal composition of claim 10, comprising the compound in which r is 5 in Formula (5) and the compound in which t is 2 in Formula (10).

13. The polymerizable liquid crystal composition of claim 10, comprising the compound in which r is 5 in Formula (5) and the compound in which t is 3 in Formula (10).

14. The polymerizable liquid crystal composition of claim 10, comprising the compound in which r is 5 in Formula (5) and the compound in which t is 4 in Formula (10).

15. The polymerizable liquid crystal composition of claim 10, further comprising at least one compound selected from the group of compounds represented by Formula (4):

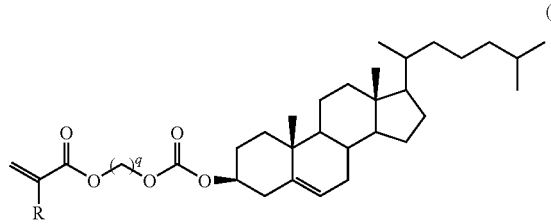

wherein q is 2, 4 or 6, and R is hydrogen or methyl.

16. The polymerizable liquid crystal composition of claim 15, comprising the compound in which r is 3 in Formula (5), the compound in which t is 3 in Formula (10) and the compound in which q is 4 in Formula (4).

17. The polymerizable liquid crystal composition of claim 15, comprising the compound in which r is 5 in Formula (5), the compound in which t is 3 in Formula (10) and the compound in which q is 2 in Formula (4).

18. A polymerizable liquid crystal composition comprising at least one compound selected from the group of compounds represented by Formula (4) and at least one compound selected from the group of compounds represented by Formula (10):

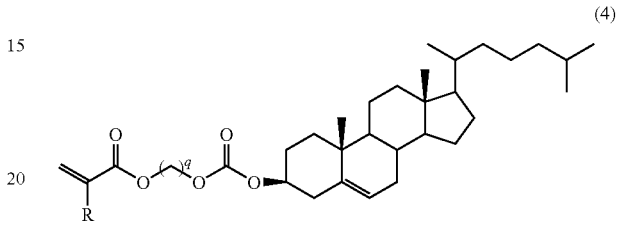

wherein q is 2, 4 or 6, and R is hydrogen or methyl; and

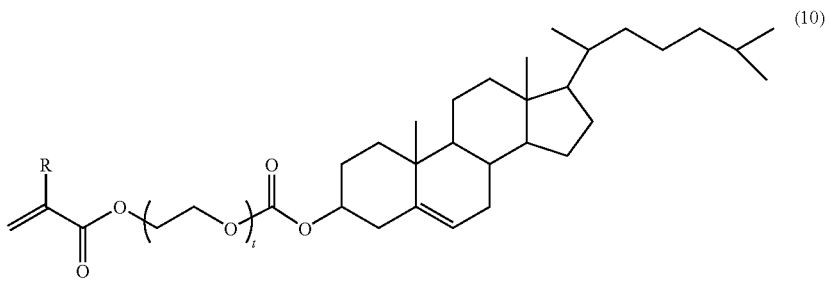

wherein t is 2, 3 or 4, and R is hydrogen or methyl.

19. The polymerizable liquid crystal composition of claim 18, comprising the compound in which q is 2 in Formula (4) and the compound in which t is 2 in Formula (10).

20. The polymerizable liquid crystal composition of claim 18, comprising the compound in which q is 2 in Formula (4) and the compound in which t is 3 in Formula (10).

21. The polymerizable liquid crystal composition of claim 18, comprising the compound in which q is 4 in Formula (4) and the compound in which t is 2 in Formula (10).

22. The polymerizable liquid crystal composition of claim 18, comprising the compound in which q is 4 in Formula (4) and the compound in which t is 3 in Formula (10).

* * * * *